United States Patent [19]

Reed et al.

[11] Patent Number: 4,637,917

[45] Date of Patent: Jan. 20, 1987

[54] BUBBLE OXYGENATOR

[76] Inventors: Charles C. Reed, 5934 Hornwood, Houston, Tex. 77036; Denton A. Cooley, 3014 Del Monte, Houston, Tex. 77019; Terry N. Crane, 2801 Precinct Line Rd., Richmond, Tex. 77469; Edward A. Swanson, 9850 S. Kirkwood, Apt. 2008, Houston, Tex. 77099; Rolf A. Oscarsson, 1550 Winchell Dr., Hudson, Ohio 44236; Vern L. Liebmann, 1460 Meadowbrook Blvd., Stow, Ohio 44224; Dan L. Cox, 14303 River Forest, Houston, Tex. 77079

[21] Appl. No.: 541,988

[22] Filed: Oct. 14, 1983

[51] Int. Cl.$^4$ .............................................. A61M 1/03
[52] U.S. Cl. ........................................ 422/46; 210/94
[58] Field of Search ................ 422/45, 46, 47; 210/94

[56] References Cited

U.S. PATENT DOCUMENTS

| Re. 27,100 | 3/1971 | DeWall | 23/258.5 |
|---|---|---|---|
| 2,652,831 | 9/1953 | Chesler | 128/214 |
| 2,721,732 | 10/1955 | Melrose | 261/83 |
| 2,833,279 | 5/1958 | Gollan | 128/214 |
| 2,854,002 | 9/1958 | DeWall et al. | 128/214 |
| 2,887,107 | 5/1959 | Wehrli | 128/214 |
| 2,896,620 | 7/1959 | Tremblay | 128/214 |
| 2,934,067 | 4/1960 | Calvin | 128/214 |
| 2,937,644 | 5/1960 | Anderson | 128/214 |
| 3,058,464 | 10/1962 | Broman | 128/214 |
| 3,065,748 | 11/1962 | Senning et al. | 128/214 |
| 3,075,524 | 1/1963 | Clark, Jr. | 128/214 |
| 3,087,490 | 4/1963 | Broman | 128/214 |
| 3,101,083 | 8/1963 | Hyman | 128/214 |
| 3,112,746 | 12/1963 | Gewecke et al. | 128/214 |
| 3,142,296 | 7/1964 | Love | 128/214 |
| 3,175,555 | 3/1965 | Ling | 128/214 |
| 3,204,631 | 9/1965 | Fields | 128/214 |
| 3,207,156 | 9/1965 | Lerman | 128/214 |
| 3,256,883 | 6/1966 | DeWall | 128/214 |
| 3,291,568 | 12/1966 | Sautter | 23/258.5 |
| 3,374,066 | 3/1968 | Farrant | 23/258.5 |
| 3,468,631 | 9/1969 | Raible et al. | 23/258.5 |
| 3,488,158 | 1/1970 | Bentley et al. | 23/258.5 |
| 3,493,347 | 2/1970 | Everett | 23/258.5 |
| 3,502,440 | 3/1970 | Tompkins | 23/258.5 |
| 3,513,845 | 5/1970 | Chesnut et al. | 128/214 |
| 3,527,572 | 9/1970 | Urkiewicz | 23/258.5 |
| 3,536,451 | 10/1970 | Ludwin | 23/258.5 |
| 3,545,937 | 12/1970 | Rozhold et al. | 23/258.5 |
| 3,547,591 | 12/1970 | Torres | 23/258.5 |
| 3,578,411 | 5/1971 | Bentley et al. | 23/258.5 |
| 3,615,238 | 10/1971 | Bentley | 23/258.5 |
| 3,640,388 | 2/1972 | Ferrari | 210/94 |
| 3,729,377 | 4/1973 | Leonard | 195/1.8 |
| 3,764,271 | 1/1972 | Brumfield | 23/258.5 |
| 3,769,162 | 10/1973 | Brumfield | 23/258.5 |
| 3,769,163 | 10/1973 | Brumfield | 195/1.8 |
| 3,770,384 | 11/1973 | Brumfield | 23/258.5 |
| 3,774,762 | 11/1973 | Lichtenstein | 210/94 |
| 3,807,958 | 4/1974 | Brumfield et al. | 23/258.5 |
| 3,827,860 | 8/1974 | Burlis | 23/258.5 |
| 3,853,479 | 12/1974 | Talonn et al. | 23/258.5 |
| 3,870,470 | 3/1975 | Yoshida et al. | 23/258.5 |
| 3,892,534 | 7/1975 | Leonard | 23/258.5 |
| 3,898,045 | 8/1975 | Bowley | 23/258.5 |
| 3,915,650 | 10/1975 | Talonn et al. | 23/258.5 |
| 3,918,912 | 11/1975 | Talonn | 23/258.5 |
| 3,960,657 | 6/1976 | Bowley | 195/1.8 |
| 3,994,689 | 11/1976 | DeWall | 23/258.5 |
| 4,033,724 | 7/1977 | Tamiya | 23/258.5 |
| 4,058,369 | 11/1977 | Bentley et al. | 23/258.5 |
| 4,065,264 | 12/1977 | Lewin | 23/258.5 |
| 4,067,696 | 1/1978 | Curtis | 23/258.5 |
| 4,073,622 | 2/1978 | Luppi | 23/258.5 |

(List continued on next page.)

Primary Examiner—Frank Spear
Attorney, Agent, or Firm—Workman, Nydegger & Jensen

[57] ABSTRACT

A bubble oxygenator for oxygenating blood in an extracorporeal circuit. The oxygenator is formed from three concentric shells which define an oxygenating chamber, a defoaming chamber and an arterial reservoir. The arterial reservoir includes a view chamber which permits visual inspection of the level of blood held in the arterial reservoir. The outer shell which forms the arterial reservoir is rotatable with respect to the remainder of the apparatus so that the view chamber can be easily positioned for observation.

33 Claims, 3 Drawing Figures

U.S. PATENT DOCUMENTS

| | | | |
|---|---|---|---|
| 4,138,288 | 2/1979 | Lewin | 195/1.8 |
| 4,138,464 | 2/1979 | Lewin | 422/46 |
| 4,140,635 | 2/1979 | Esmond | 210/177 |
| 4,158,693 | 6/1979 | Reed et al. | 422/46 |
| 4,160,801 | 7/1979 | Badolato et al. | 422/46 |
| 4,180,896 | 1/1980 | Reed et al. | 29/157 R |
| 4,182,739 | 1/1980 | Curtis | 422/47 |
| 4,183,961 | 1/1980 | Curtis | 424/366 |
| 4,188,360 | 2/1980 | Kurata | 422/46 |
| 4,203,944 | 5/1980 | DeWall | 422/47 |
| 4,203,945 | 5/1980 | DeWall | 422/47 |
| 4,205,042 | 5/1980 | Lobdell et al. | 422/47 |
| 4,228,125 | 10/1980 | Lobdell et al. | 422/46 |
| 4,239,728, | 12/1980 | Stenberg et al. | 422/46 |
| 4,248,828 | 2/1981 | Bentley et al. | 422/47 |
| 4,261,951 | 4/1981 | Milev | 422/46 |
| 4,268,476 | 5/1981 | Raible | 422/46 |
| 4,272,373 | 6/1981 | Stenberg et al. | 210/175 |
| 4,280,981 | 7/1981 | Harnsberger | 422/46 |
| 4,282,180 | 8/1981 | Raible | 422/46 |
| 4,297,318 | 10/1981 | Raible | 422/46 |
| 4,336,224 | 6/1982 | Siposs | 422/46 |
| 4,372,914 | 2/1983 | Raible | 422/46 |

BUBBLE OXYGENATOR

Background

1. The Field of the Invention

The present invention relates to blood oxygenators used in extracorporeal circuits and, more particularly, to a novel bubble oxygenator which is compact, relatively inexpensive to build and which has a relatively low internal volume.

2. The Prior Art

Many types of heart surgery require the use of a cardiopulmonary bypass circuit to take over the functions of the heart and lungs while the needed surgery is being performed. Three of the basic components of a cardiopulmonary bypass circuit are a pump which forces the blood through the circuit and back into the patient's body, a heat exchanger which is used to adjust the temperature of the blood before reinjection, and an oxygenator which adds oxygen to the blood while it removes carbon dioxide. In many devices, the heat exchanger and oxygenator are combined into a single unit to minimize the number of tubing connections which must be made and to decrease the liquid volume requirements of the system.

Several different processes have been used in oxygenators to cause oxygenation of the blood. One process involves the use of a permeable membrane which separates the blood from the oxygen but which allows gas exchange to take place by diffusion through the membrane. A second process which has been developed exposes a thin film of blood to an oxygen atmosphere such that gas transfer can occur. A third, and the most commonly used, process of oxygenation involves mixing small bubbles of an oxygen rich gas with the blood such that the oxygen can be absorbed.

Although many different types of bubble oxygenators have been developed, typically all bubble oxygenators have three distinctly identifiable sections: an oxygenating section, a defoaming section, and an arterial reservoir.

Oxygen and other gases are introduced into the oxygenating section through small tubes or a porous member. Each small tube or porous member creates small bubbles which are dispersed in the blood. As the gases and blood are mixed together, oxygen is absorbed by the blood and carbon dioxide is liberated. In most devices, the majority of the oxygenation takes place in this section. However, in some devices the blood has a short residence time in the oxygenating section; thus, oxygenation continues to occur as the blood passes through the subsequent defoaming section.

As oxygen is bubbled through the blood in a bubble oxygenator, a certain amount of foaming necessarily occurs. This foam, and any entrapped air bubbles, must be removed from the blood before it is reinjected into the patient; otherwise, the entrapped air bubbles can form an embolus which can severely injure or kill the patient. Defoaming is generally accomplished by passing the blood over a material having a large surface area which has been treated with a defoaming agent. This large surface area can be provided by stainless steel wool, polyurethane foam, or other suitable materials. Numerous types of defoaming agents are known in the art and can be applied to the material which is used to provide the large surface area.

The arterial reservoir provides an area where the defoamed blood is collected before reinjection into the patient. The reservoir acts as a safety feature in helping avoid accidental pumping of air into the blood lines. Should the blood supply to the oxygenator be accidently stopped, the reservoir must contain sufficient blood to allow the perfusionist to stop the output from the oxygenator before air enters the arterial line. To this end, the reservoir should hold sufficient blood to supply the patient for twenty or forty seconds at the perfusion flow rate. Monitoring the level of blood in the arterial reservoir is thus a critical factor and is one of the major problems encountered in using bubble oxygenators. In some prior art devices, a heat exchanger is included in the arterial reservoir to regulate the temperature of the blood before reinjection. However, this makes it difficult to observe the blood level in the reservoir.

While the margin of safety could be increased by simply increasing the size of the arterial reservoir, this approach has several definite disadvantages. First, large reservoirs significantly increase the amount of blood needed to prime the oxygenator. This means that either more blood must be taken from the patient, or more substitute blood must be added to the system which increases the chance that an adverse reaction in the blood can occur. Second, larger reservoirs increase the residence time of the blood in the oxygenator which increases the possibility of hemolysis.

Even if the arterial reservoir does not run dry, air can enter the arterial line if a vortex flow is created in the arterial reservoir. In order to avoid this, many prior art devices have included a complicated series of baffles in the arterial reservoir to prevent the formation of a vortex. However, the presence of these baffles also increases the likelihood of hemolysis occurring and makes it more difficult to monitor the blood level.

Accordingly, what is needed in the art is a bubble oxygenator which is simple and inexpensive to construct yet provides an efficient means for oxygenating the blood. It would be a further advancement in the art to provide such a device which has a low internal volume so as to decrease the amount of blood which must be removed from the patient and to decrease the residence time of the blood yet includes an arterial reservoir which is easy to monitor and control so as to provide a margin of safety to prevent air bubbles from being injected into the patient. Such a device is disclosed and claimed herein.

OBJECTS AND BRIEF SUMMARY OF THE INVENTION

It is a primary object of the present invention to provide a bubble oxygenator which has a novel concentric configuration which provides a low internal volume yet provides a margin of safety against having air enter the arterial line.

It is a further object of this invention to provide a bubble oxygenator having an arterial reservoir which provides the perfusionist with an unobstructed view of the blood in the reservoir, and which helps to prevent air from becoming entrained in the blood as it exits the reservoir.

It is another object of the present invention to provide a disposable oxygenator having a configuration that is inexpensive and simple to construct.

It is still a further object of the present invention to provide a bubble oxygenator which includes a view chamber in the arterial reservoir for observing the blood level and wherein the position of the view chamber can be easily changed to facilitate observation.

These and other objects and features of the present invention will become more fully apparent from the following description and appended claims taken in conjunction with the accompanying drawings.

In accordance with the foregoing objects, the present invention provides a novel bubble oxygenator for use in cardiopulmonary bypass circuits.

In one preferred embodiment, the oxygenator of the present invention utilizes a series of three concentric annular chambers to process the blood. The blood is introduced into the oxygenator through a conduit which leads to the bottom of the innermost concentric chamber where it is mixed with small bubbles of oxygen which are formed by passing the oxygen through a sparging plate. The mixture of blood and gas then flows upwardly past a heat exchanger that is centered within the inner chamber and which is utilized to control the temperature of the blood. After passing the heat exchanger, the blood flows into the top of the second concentric chamber which is filled with a polyurethane sponge which has been treated with a suitable defoaming agent. As the blood passes downwardly through the polyurethane sponge, the air bubbles are removed from the foam.

The defoaming section is generally funnel shaped having a cylindrical upper portion which surrounds the inner chamber where oxygenation occurs and a lower spout portion. Because the blood enters the top of the defoaming section and then flows downwardly, it will be required to pass through a pre-determined amount of defoamer before entering the arterial reservoir area. As the blood passes through the defoaming section, it exits through holes in the sides of the spout portion into the third chamber which serves as the arterial reservoir.

The arterial reservoir is divided into upper and lower sections. The upper section is generally cylindrical in shape and surrounds the defoaming section so as to leave an annular space therebetween. The lower section of the arterial reservoir has a cylindrical center portion which surrounds the spout of the defoaming section and is coaxial therewith, and a view chamber which extends outwardly from one side of the lower cylindrical portion. The view chamber is generally rectangular in shape and it is longitudinally coextensive with the lower cylindrical portion of the arterial reservoir. As blood fills the arterial reservoir, the level of the blood can easily be viewed in the view chamber so as to monitor the blood level.

The arterial outlet of the oxygenator is located in the bottom of the view chamber. Because of the narrow shape of the view chamber, the chamber acts as a deterrent to eliminate any vortex action which could cause air to become entrained in the arterial line along with the blood.

The arterial reservoir is connected to the top of the oxygenator such that it can be rotated during use to provide the perfusionist with a clear, unobstructed view of the view chamber. The entire apparatus is designed to be easily and inexpensively fabricated such that it can be disposed of after use.

BRIEF DESCRIPTION OF THE DRAWINGS

Reference is next made to the drawings, in which like parts are designated with like numerals throughout, and in which.

DETAILED DESCRIPTION OF THE PREFERRED EMBODIMENT

Figure 1:
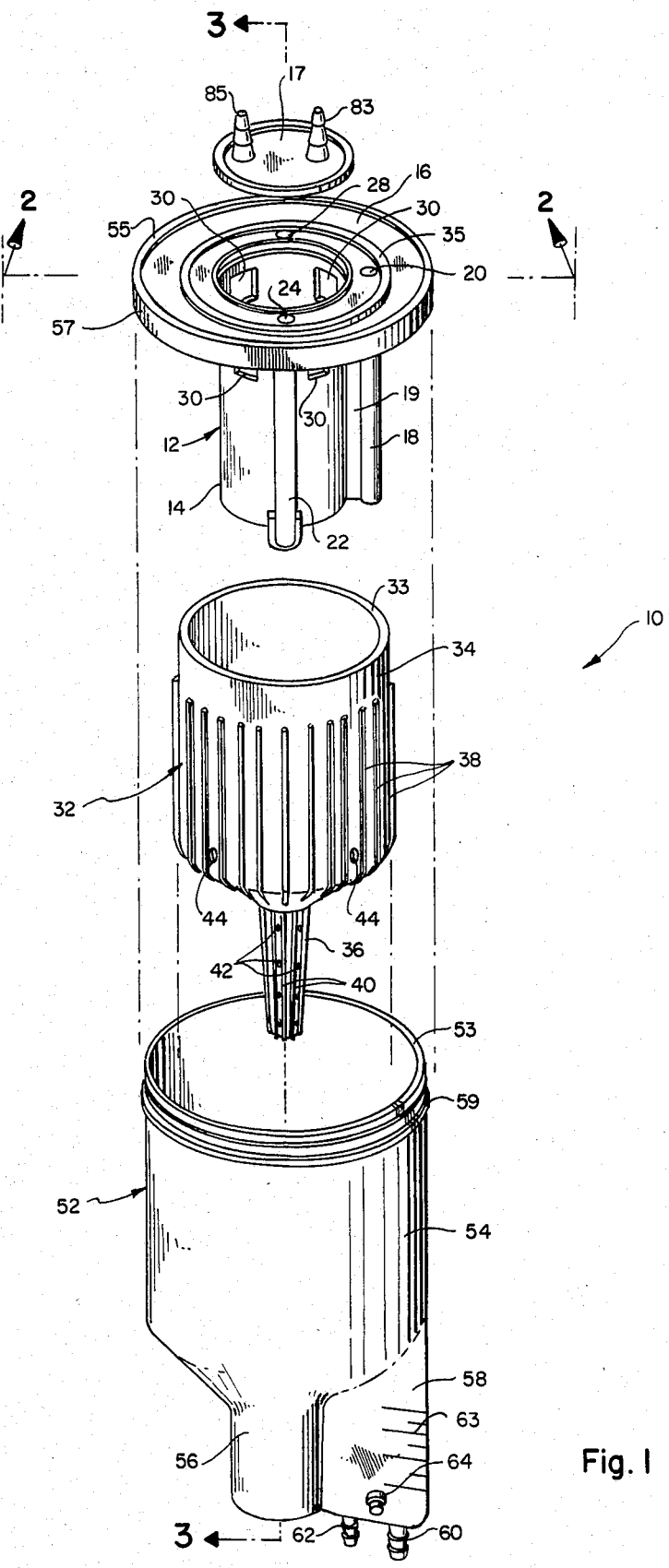
FIG. 1 is an exploded perspective view of the bubble oxygenator of the present invention.

Reference is first made to FIG. 1 which illustrates the principal components of a preferred embodiment of the oxygenator of the present invention, generally designated at 10, in an exploded perspective view.

Oxygenator 10 includes three annular chambers which are formed from three concentric shells generally designated at 12, 32 and 52. The inner shell 12 has a cylindrical body 14 which defines the outer wall of an annular space 31 (see FIG. 2) which, as hereinafter more fully explained, serves as the oxygenating chamber. A lid 16 extends radially outward from the top of body 14. A second lid 17 fits on the top of body 14 to seal the top of the innermost chamber. As also discussed more fully hereinafter, the remaining shells 32 and 52 are secured in annular grooves which are formed on the underside of ridges 35 and 55 such that lid 16 seals the annular spaces between the three shells 12, 32 and 52. The annular space between shells 12 and 32 serves as a defoaming chamber, while the annular space between shell 32 and 52 serves as an auxiliary arterial reservoir, as more fully described in connection with FIGS. 2 and 3, below.

An oxygen inlet tube 18 is molded as an integral part of the oxygenator along one side of cylindrical body 14 to direct an oxygen rich gas to the bottom of the inner chamber. Tube 18 is molded so as to be attached to body 14 by a web 19, and contains no joints since it is molded integrally with body 14. Advantageously, this eliminates areas for leaks. An inlet port 20 is formed in lid 16 to correspond to the top of tube 18.

A first blood inlet tube 22 is formed longitudinally along the side of body 14 and is circumferentially spaced ninety degrees from oxygen inlet tube 18. Tube 22 includes an inlet port 24 formed in lid 16. A second blood inlet tube 26 (see FIG. 3) is formed on the side of body 14 opposite tube 22. Tube 26 also includes an inlet port 28 which is formed in lid 16. Each of the holes 20, 24 and 28 may be covered by a removable microbial tape (not shown) to help maintain the oxygenator in a sterile condition prior to use.

Blood inlet tubes 22 and 26 are utilized to introduce blood into the bottom of the oxygenating chamber which is formed within the center of body 14. One of the inlet tubes can be connected to the venous catheter (not shown) which is attached to the patient and the other inlet tube can be connected to a cardiotomy reservoir (not shown) if one is used in the extracorporeal circuit.

A plurality of apertures 30 are formed around the top of body 14 to provide openings through which the blood can flow to pass from the inner oxygenating chamber to the defoaming chamber. In the illustrated embodiment, apertures 30 have a generally rectangular shape. However, it will readily be appreciated that other configurations could serve equally as well.

The middle shell 32 which forms the outer wall of the defoaming chamber is generally funnel-shaped in configuration and is designed to encompass inner shell 12 and inlet tubes 18, 22, and 26. The annular space 51 (see FIGS. 2 and 3) defined between shell 22 and 32 is filled with a suitable material 86 such as polyurethane foam or stainless steel wool which has been treated with a suitable defoaming agent for removing air bubbles from the blood.

Referring still to FIG. 1, shell 32 has a cylindrically shaped upper portion 34 and a lower tapered spout portion 36. A plurality of vertical ribs 38 are spaced around the outer surface of upper cylindrical portion 34 of shell 32. Similarly, a plurality of ribs 40 are vertically formed around spout 36. As discussed more fully hereinafter, ribs 38 and 40 are used to space a filter membrane (indicated at 90 in FIGS. 2 and 3) which fits over the outer surface of shell 32. The filter membrane is of a one-piece construction and filters any large particulate matter or entrapped air bubbles from the blood as it passes from the defoaming chamber into the arterial reservoir. The filter membrane also eliminates a seal at the bottom which could allow embolus-forming air bubbles to escape.

Holes 42 and 44 are formed in spout 36 between ribs 40 and in the bottom of the upper cylindrical portion 34 of shell 32 in order to allow the blood to pass from the defoaming chamber into the arterial reservoir which is formed by the space between the spout 36 of shell 32 and the outer shell 52. As shown best in FIGS. 2 and 3, the upper edge 33 of shell 32 is secured within an annular groove formed in lid 16 on the underside of ridge 35 to hold shells 12 and 32 in position with respect to each other and to prevent foam from flowing over the top of shell 32 and into the arterial reservoir.

Figure 2:
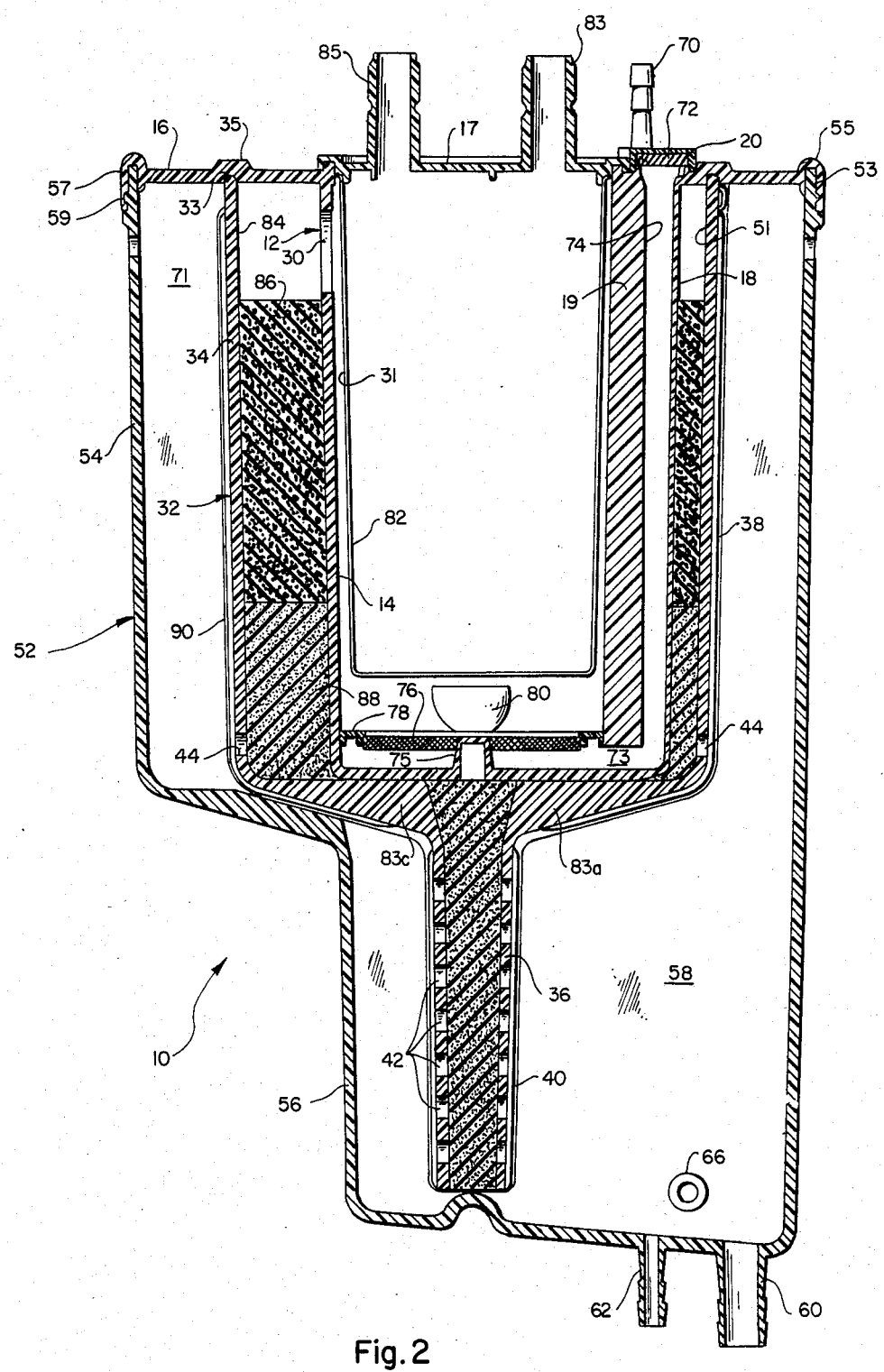
FIG. 2 is a longitudinal cross-sectional view of a fully assembled oxygenator taken at the position indicated by line 2—2 of FIG. 1.
Figure 3:
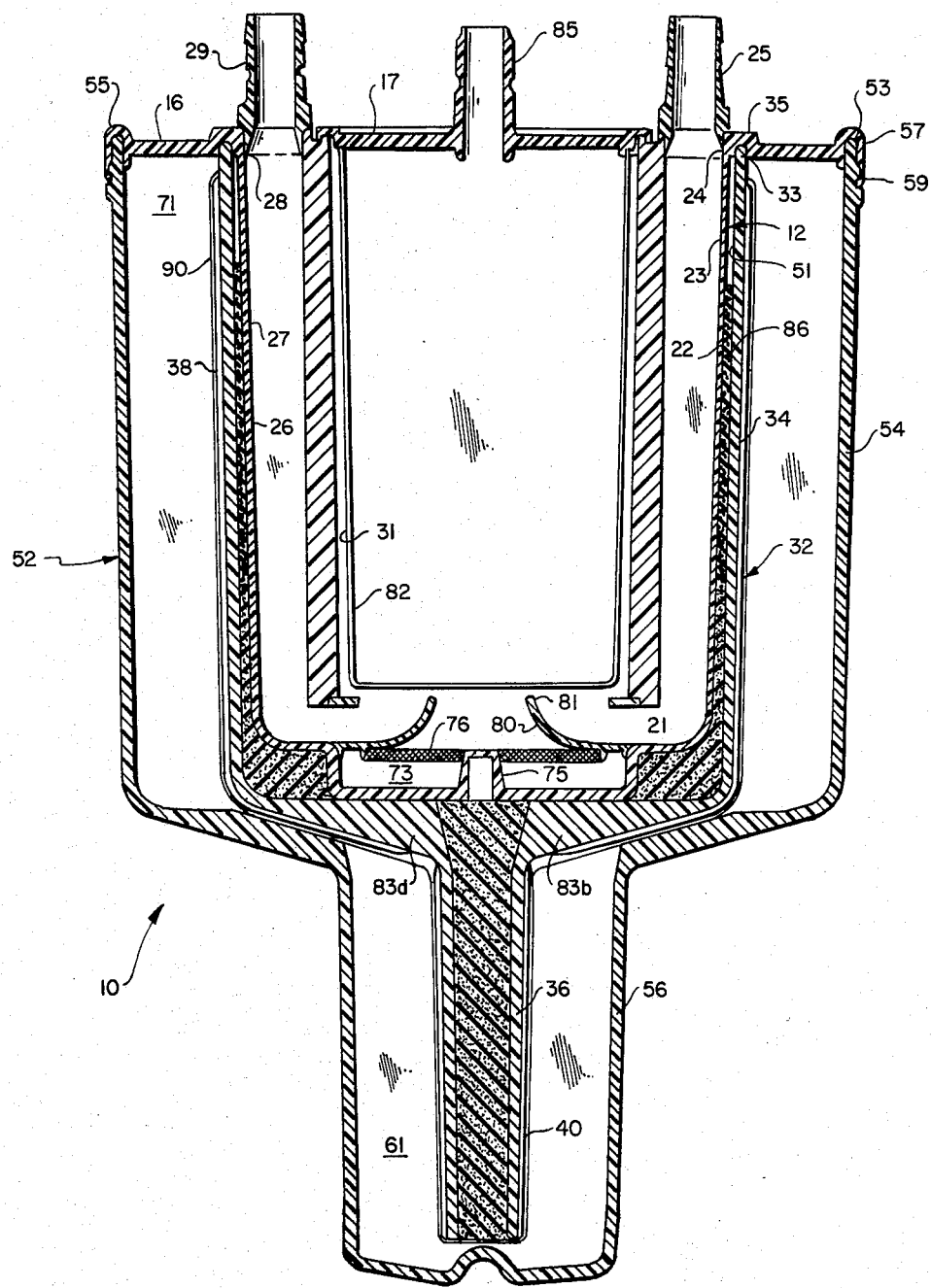
FIG. 3 is a longitudinal cross-sectional view of a fully assembled oxygenator taken at the position indicated by line 3—3 of FIG. 1.

Outer shell 52 includes an upper portion 54 which is generally cylindrical in shape and which is sized such that it creates an annular space 71 (see FIGS. 2 and 3) around cylindrical portion 34 of shell 32. The annular space 71 serves as an auxiliary arterial reservoir. As shown in FIGS. 2 and 3, the top edge 53 of shell 52 fits within an annular groove formed on the underside of ridge 55 in lid 16. Shell 52 is secured to lid 16 by a snap fit relationship provided by the outer edge 57 of lid 16, which has a groove designed to receive in locking relationship a corresponding ridge 59 formed on the upper edge of outer shell 52. Thus, shell 52 can be rotated with respect to the lid 16, as described more fully below.

The lower portion of shell 52 serves as the main arterial reservoir and includes a cylindrical portion 56 which surrounds spout 36 and is coaxial with upper portion 54. The arterial reservoir also includes a view chamber 58 which is adjacent cylindrical portion 56. View chamber 58 is relatively narrow and has a generally rectangular-shaped cross section so that the blood level therein will change at a more or less constant rate as blood enters or leaves the arterial reservoir. Chamber 58 is in fluid communication along one side with cylindrical portion 56.

The sides of view chamber 58 are formed from a transparent material and is provided with suitable markings 63 (see FIG. 1) so that the volume of blood in the arterial reservoir can easily be monitored. Additionally, inasmuch as shell 52 can be rotated with respect to lid 16, view chamber 58 can be easily positioned for observation by the perfusionist.

An outlet port 60 is formed in the bottom of view chamber 58 to allow the oxygenated blood to be removed for injection back into the patient. A second outlet port 62 can also be formed in the bottom of chamber 58 to allow oxygenated blood to be pumped into a coronary line. Advantageously, the relatively narrow rectangular shape of view chamber 58 acts as a deterrent to the formation of a vortex as blood exits through ports 60 and 62, thus decreasing the likelihood that air will be entrained in the blood as it enters into the lines leading to the patient.

A sampling port 64 is formed on one side of chamber 58 and is provided with a luer fitting such that samples of the oxygenated blood can easily be withdrawn for testing. Additionally, another port (not shown) is formed on the other side of chamber 58 opposite from port 64 so that the temperature of the blood can be monitored by a temperature probe inserted into the port.

Having briefly described the major components of oxygenator 10 with respect to FIG. 1, reference is now made to FIGS. 2 and 3 which are cross-sectional views of the fully assembled oxygenator 10. With particular reference to FIG. 2, a coupling 70 is positioned on the top of oxygenator 10 for connection to a tube leading to an oxygen source. Coupling 70 is offset a small distance from inlet port 20 such that a filter 72 can be placed therebetween to remove any foreign particles which may be entrained in the stream of oxygen.

As it enters oxygenator 10, the oxygen passes down through the bore 74 of tube 18 to the space 73 provided at the bottom of body 14. A sparger plate 76 which is designed to create small oxygen bubbles for mixing the oxygen with the blood is positioned in the bottom of cylindrical body 14 and is retained in place by a ring 78 and is supported at its center by a post 75. The oxygen is mixed with the blood which is introduced into the bottom of body 14 above sparger plate 76.

As shown best in FIG. 3, a coupling 25 is positioned at inlet port 24 such that oxygenator 10 can be connected to a line containing blood taken from a vein of the patient. The blood travels through the hollow of inlet tube 22 and is introduced into the bottom of body 14 of shell 12. The blood is introduced above sparger plate 76 where it is allowed to mix with the oxygen bubbles such that oxygenation can occur. A deflector 80 (see also FIG. 2) is positioned in the bottom of body 14 so as to prevent oxygen from flowing back up through the blood inlet tube 22. Since the end 81 of deflector 80 is slightly higher than the bottom 21 of tube 22, the gaseous bubbles will tend to travel along the bottom of heat exchanger 82 and then into the annular space 31 which forms the oxygenating chamber.

A second coupling 29 is positioned at the top of the second blood inlet port 28 so that oxygenator 10 can be connected to a cardiotomy reservoir if one is utilized in the extracorporeal circuit. The blood from the cardiotomy reservoir travels through the hollow of blood inlet tube 26 and is also introduced into the bottom of body 14. After the blood is mixed with the oxygen it moves upwardly through the annular space 31 to the openings 30 formed at the top of body 14. The heat exchanger 82 is sealed in a fluid-tight manner around its upper periphery so that the blood is not mixed with the water or other heating fluid circulated through the heat exchanger.

As schematically illustrated in FIGS. 2 and 3, a heat exchanger 82 is positioned within cylindrical body 14. Water or other suitably heated fluid is pumped through heat exchanger 82 through couplings 83 and 85 (see FIG. 2) to regulate the temperature of the blood as it passes upwardly through space 31.

Heat exchanger can be 82 of any conventional design so long as it is configured to fit within body 14. Heat exchanger 82 must be sized so as to form sufficient space to allow the oxygenated blood to pass upwardly to the top of the inner chamber at a sufficient rate of flow to permit the blood to be heated to the desired temperature. Significantly, by including heat exchanger 82 in oxygenator 10 rather than as a separate unit the volume of blood needed to prime the extracorporeal circuit is reduced, as is the number of tube couplings.

As the blood rises in the oxygenating chamber defined by space 31, oxygenation of the blood and liberation of carbon dioxide occurs. When the oxygenated blood reaches the top of the chamber, it passes through apertures 30 where it enters the defoaming chamber defined by annular space 51 between shells 12 and 32. In the preferred embodiment, the upper portion of the defoaming chamber is filled with a 20 ppi polyurethane sponge, as indicated at 86. The lower portion of the defoaming chamber, including the center of spout 36, is filled with an 80 ppi polyurethane sponge 88. Thus, as the blood flows downwardly through the polyurethane sponge under the force of gravity, the air bubbles are removed from the blood before it enters the arterial reservoir. The blood exits the defoaming chamber through apertures 44 and 42 which are formed in the sides of the shell 32, and then passes through the filter membrane 90. Filter membrane 90 is a 105 micron polyester filter placed over the shell 32 and spaced therefrom by ribs 38 and 40 (see FIG. 1) as described above.

Filter membrane 90 filters out any entrapped air bubbles which are not removed as the blood passes through the polyurethane sponge and any particulate matter greater than about 100 microns in diameter which is in the blood. Accordingly, the blood which enters the arterial reservoir for return to the patient is essentially free of any matter which could seriously harm the patient.

In the illustrated embodiment, four vertical ribs 83a–83d are formed in the interior and at the bottom of cylindrical portion 34 of shell 32. The body 14 of inner shell 12 sits on ribs 83a–83d so that blood can flow between the ribs to the lower spout portion 36 of the middle shell 32.

After being oxygenated and defoamed, the blood is held in the arterial reservoir formed by the lower cylindrical portion 56 (see FIG. 1) and view chamber 58 of outer shell 52 before it is reinjected into the patient. It is important to maintain a level of blood in the arterial reservoir which is sufficient to allow the perfusionist to stop the outflow of blood to prevent air from entering the patient should the inflow of blood into the oxygenator be stopped for any reason. In the prior art devices, it has been difficult for the perfusionist to monitor the level of blood. For example, in some of the prior art devices the level of blood was hard to observe because of obstructions in the reservoir, thus making the blood level difficult to control. In other prior art devices, the blood level could change rapidly or erratically because of the shape of the reservoir.

The present invention provides an oxygenator which overcomes these problems of the prior art devices. In oxygenator 10, the reservoir of blood is maintained in the annular space 61 (see FIG. 3) between spout 36 and the lower cylindrical portion 56 of outer shell 52, and in the space provided by view chamber 58 (see FIG. 2). As discussed previously with reference to FIG. 1, view chamber 58 is generally rectangular in cross-section and is formed from a transparent material such as clear plastic to allow the perfusionist to see the blood level without any obstructions. Thus, it is easy to monitor the level of blood in the view chamber 58. Additionally, outer shell 52 is rotatable with respect to lid 16 such that shell 52 can be positioned so that view chamber 58 is directly visible to the perfusionist. Also, the cross-sectional area of view chamber 58 and the annular space 61 in lower cylindrical portion 56 is substantially uniform. Accordingly, the level of blood in the arterial reservoir rises and falls at a substantially uniform rate when the blood flow rate is constant.

Another advantage of the present invention relates to the position at which blood is removed from the arterial reservoir through outlet 60 which is formed in the bottom of view chamber 58. Because of the narrowness of view chamber 58, the view chamber 58 acts to prevent the formation of a vortex which could cause air to be entrained in the blood as it exits through outlet 60 and into the line leading to the patient. A second outlet 62 to which a coronary line can be attached is also positioned at the bottom of view chamber 58.

The upper cylindrical portion of outer shell 52 forms the oer wall of an annular space 71 which serves as an auxiliary arterial reservoir, and which provides an added margin of safety if the inflow of blood to the oxygenator is interrupted for any reason.

The invention may be embodied in other specific forms without departing from its spirit or essential characteristics. The described embodiment is thus to be considered in all respects only as illustrative and not restrictive. The scope of the invention is, therefore, indicated by the appended claims rather than by the foregoing description. All modifications or changes which come within the meaning and range of equivalency of the claims are to be embraced within their scope.

What is claimed and desired to be secured by United States Letters Patent is:

1. An apparatus for oxygenating blood comprising:
    a first shell defining a first chamber wherein venous blood can be mixed with bubbles of an oxygen rich gas such that oxygenation of the blood can occur;
    a second shell concentric to said first shell and spaced therefrom so as to form a second chamber wherein air bubbles can be removed from the oxygenated blood after oxygenation has occurred; and
    a third shell concentric to said second shell and spaced therefrom so as to define a third chamber which serves as an arterial reservoir for holding a quantity of oxygenated blood for reinjection into the patient, said third chamber comprising a view chamber having a first generally planar side formed from a substantially transparent material and a second side, wherein the two sides are spaced relatively close together in relation to their height and width such that the sides deter the formation of a vortex as blood flows through the third chamber, said third chamber further having a generally uniform cross-sectional area such that the level of blood observed in the view chamber rises or falls at a substantially constant rate when blood is added to or withdrawn from said reservoir.

2. An apparatus as defined in claim 1 wherein said first shell comprises a first tube molded thereto for introducing said gas into the interior of said first shell, and a second tube for introducing said venous blood into the interior of said first shell.

3. An apparatus as defined in claim 2 wherein said first shell further comprises a lid extending radially outward from the top of the sides of said first shell, said lid being connected to said second shell and said third shell so as to seal the top of said second and third chambers one from the other, thereby reducing possible introduction of an embolus-forming air bubble into said oxygenator.

4. An apparatus as defined in claim 3 wherein said lid comprises a first connector for attaching said first tube to a source of said oxygen rich gas, and a second connector for attaching said second tube to an extracorporeal circuit for delivering said venous blood from a patient.

5. An apparatus as defined in claim 4 further comprising a heat exchanger positioned concentrically within the interior of said first shell and spaced therefrom so as to form an annular space between said first shell and said heat exchanger which serves as said first chamber.

6. An apparatus as defined in claim 5 further comprising a second lid for enclosing said heat exchanger within said first shell.

7. An apparatus as defined in claim 6 wherein said second lid comprises first and second connectors for attachment to a source of heated fluid.

8. An apparatus as defined in claim 1 wherein said first shell further comprises a sparger plate positioned in the lower portion thereof such that said gas will exit as small bubbles as it passes therethrough into said first chamber.

9. An apparatus as defined in claim 1 wherein said first shell comprises a plurality of apertures formed in the sides thereof such that oxygenated blood can pass from the first chamber into the second chamber through said apertures.

10. An apparatus as defined in claim 1 further comprising a material positioned in said second chamber and coated with a defoaming agent such that air bubbles are removed from blood passing through the second chamber.

11. An apparatus as defined in claim 10 wherein said material comprises a polyurethane sponge.

12. An apparatus as defined in claim 1 wherein said second shell is generally funnel shaped in configuration having a cylindrical upper portion and a spout shaped lower portion.

13. An apparatus as defined in claim 12 wherein said second shell further comprises a plurality of apertures formed in said spout portion such that blood can pass from said second chamber into said third chamber through said apertures.

14. An apparatus as defined in claim 1 wherein said second shell further comprises a plurality of ribs formed on the outer surface thereof.

15. An apparatus as defined in claim 14 further comprising a filter membrane substantially conforming to the shape of the outer surface of said second shell and spaced therefrom by said ribs.

16. An apparatus as defined in claim 1 comprising means for rotating said third shell relative to said first and second shells such that said view chamber can be easily positioned for observation.

17. An apparatus as defined in claim 1 further comprising an outlet port formed on said view chamber, and wherein said view chamber is configured to prevent the formation of a vortex as blood exits through said outlet port.

18. An apparatus as defined in claim 1, wherein said second side is generally planar and is formed from a substantially transparent material, said second side being substantially parallel to said first side.

19. An apparatus as defined in claim 18, wherein said view chamber further comprises an outlet port positioned at the base of said view chamber.

20. A bubble oxygenator for oxygenating blood from a patient in an extracorporeal circuit, said oxygenator comprising:
means for forming an oxygenating chamber wherein venous blood is mixed with bubbles of an oxygen rich gas such that oxygenation of the blood can occur;
means for forming a defoaming chamber adjacent said oxygenating chamber wherein air bubbles can be removed from the blood after oxygenation has occurred; and
means for forming a reservoir of oxygenated blood for reinjection into the patient, said means for forming said reservoir comprising a view chamber formed therein for monitoring the level of blood in said reservoir, said view chamber having a first generally planar side formed from a substantially transparent material and a second side, wherein the two sides are spaced relatively close together in relation to their height and width such that the sides deter the formation of a vortex as blood flows through the view chamber, said view chamber having a generally uniform cross-sectional area such that the level of blood observed in the view chamber rises or falls at a substantially constant rate when blood is added to or withdrawn from said reservoir, and further comprising means for rotating said view chamber relative to said oxygenating and defoaming chambers such that the view chamber can be easily rotated to a convenient position for monitoring the blood level.

21. A bubble oxygenator as defined in claim 20 wherein said view chamber comprises a generally planar first side formed from a substantially transparent material and a generally planar second side formed from a substantially transparent material, said second side being substantially parallel to said first side.

22. An apparatus as defined in claim 21, wherein the two generally planar sides are spaced relatively close together in relation to their height and width, and further including an outlet port positioned at the base of said view chamber so that blood exiting from the view chamber will not form a vortex.

23. A bubble oxygenator as defined in claim 20 further comprising a heat exchanger concentrically positioned within said first shell and spaced therefrom so as to form an annular space between said first shell and said heat exchanger.

24. A bubble oxygenator as defined in claim 20 further comprising a lid attached to the top of the sides of said first shell and extending radially outward therefrom, said lid comprising means for receiving said second and third shells in sealing engagement so as to enclose the top of the annular space between said first and second shells from the annular space formed between said second and third shells.

25. An apparatus for oxygenating blood comprising:
a first shell;
a heat exchanger concentrically spaced from said first shell so as to form an annular space between said first shell and said heat exchanger which serves as an oxygenating chamber;

first means for introducing venous blood into said oxygenating chamber;

second means for introducing an oxygen rich gas into said oxygenating chamber;

a second shell concentrically spaced from said first shell so as to form an annular space between said first and second shells which serves as a defoaming chamber, said defoaming chamber being substantially filled with a quantity of essentially porous material treated with a defoaming agent; and a third shell concentrically spaced from said second shell so as to form an annular spaced between said second and third shells which serves as an arterial blood reservoir, and third shell comprising means for forming an essentially transparent view chamber for visually observing the level of blood in said reservoir, said view chamber having substantially parallel planar sides and having a generally uniform cross-sectional area such that the level of blood in the view chamber and the annular space between the second and third shells arises or falls at a substantially constant rate when blood is added to or withdrawn therefrom, said parallel planar sides being spaced relatively close together in relation to their height and width such that the sides deter the formation of a vortex as blood flows through the third shell.

26. An apparatus as defined in claim 25 wherein said first means comprises a first tube for introducing said oxygen rich gas into the interior of said first shell near the bottom thereof, and wherein said second means comprises a second tube for introducing said venous blood into the interior of said first shell near the bottom thereof.

27. An apparatus as defined in claim 26 further comprising means positioned in the interior of said first shell near the bottom thereof for deflecting gas bubbles introduced through said tube so that said gas bubbles will not travel back through said second tube.

28. An apparatus as defined in claim 25 wherein said first shell comprises a lid attached at the top of the sides of said first shell, said lid extending radially outward therefrom and comprising means for receiving in sealing engagement the top edges of said second and third shells so as to enclose the top of each annular space formed between said first, second and third shells.

29. An apparatus as defined in claim 28 wherein said lid further comprises means for receiving the top edge of said third shell in a snap-fit relationship so as to permit said third shell to be rotated relative to said lid.

30. An apparatus as defined in claim 25 wherein said second shell is generally funnel shaped and comprises an upper cylindrical portion and a lower spout portion, and wherein said lower spout portion is provided with a plurality of apertures through which blood exits from said defoaming chamber into said arterial blood reservoir.

31. An apparatus as defined in claim 25 wherein said second shell comprises a plurality of ribs spaced about the outer surface of said second shell, and wherein said apparatus further comprises a filter membrane which fits over the outer surface of said second shell and is spaced therefrom by said ribs.

32. An apparatus as defined in claim 25 wherein said arterial blood reservoir and said view chamber comprise an essentially uniform cross-sectional area such that the level of blood held in said reservoir and said view chamber will uniformly rise or fall in accordance with the flow rate at which blood enters or exits therefrom.

33. An apparatus as defined in claim 25 wherein said view chamber comprises a relatively thin cross-sectional area and wherein said apparatus comprises an outlet port positioned at the base of said view chamber whereby blood exiting from said view chamber will not form a vortex because of the cross-sectional shape of said view chamber.

* * * * *

UNITED STATES PATENT AND TRADEMARK OFFICE
CERTIFICATE OF CORRECTION

PATENT NO. : 4,637,917

DATED : January 20, 1987

INVENTOR(S) : Charles C. Reed, Denton A. Cooley, Terry N. Crane, Edward A. Swanson, Rolf A. Oscarsson, Vern L. Liebmann, Dan L. Cox It is certified that error appears in the above-identified patent and that said Letters Patent are hereby corrected as shown below:

Col. 7, line 1, "Heat exchanger can be 82 of" should be --Heat exchanger 82 can be of--

Col. 8, line 24, "oer" should be --outer--

Signed and Sealed this

Twenty-eighth Day of April, 1987

Attest:

DONALD J. QUIGG

Attesting Officer

Commissioner of Patents and Trademarks